United States Patent
Eguchi et al.

(10) Patent No.: US 8,183,368 B2
(45) Date of Patent: May 22, 2012

(54) THERMOSETTING COMPOUND, COMPOSITION CONTAINING THE SAME, AND MOLDED ARTICLE

(75) Inventors: Yuji Eguchi, Tsukuba (JP); Kazuo Doyama, Tsukuba (JP); Shigeki Nomura, Tsukuba (JP); Hatsuo Ishida, Tsukuba (JP)

(73) Assignee: Sekisui Chemical Co., Ltd., Osaka (JP)

( * ) Notice: Subject to any disclaimer, the term of this patent is extended or adjusted under 35 U.S.C. 154(b) by 764 days.

(21) Appl. No.: 11/997,998

(22) PCT Filed: Aug. 3, 2006

(86) PCT No.: PCT/JP2006/315372
§ 371 (c)(1),
(2), (4) Date: Feb. 19, 2009

(87) PCT Pub. No.: WO2007/018110
PCT Pub. Date: Feb. 15, 2007

(65) Prior Publication Data
US 2009/0299062 A1    Dec. 3, 2009

(30) Foreign Application Priority Data
Aug. 5, 2005   (JP) .................................. 2005-228737

(51) Int. Cl.
*C07D 413/02* (2006.01)
*C08G 14/06* (2006.01)
*C07D 413/00* (2006.01)
*C08G 14/00* (2006.01)

(52) U.S. Cl. ........................... 544/73; 528/129; 528/145
(58) Field of Classification Search .................... 544/73; 528/129, 145
See application file for complete search history.

(56) References Cited

U.S. PATENT DOCUMENTS
5,543,516 A   8/1996 Ishida
2004/0068084 A1   4/2004 Hwang et al.

FOREIGN PATENT DOCUMENTS

| JP | S49-47378 A | 5/1974 |
| JP | 08-183835 A | 7/1996 |
| JP | 9-502452 A | 8/1996 |
| JP | 11-106466 A | 4/1999 |
| JP | 2000-154225 A | 6/2000 |
| JP | 2003-082099 A | 3/2003 |
| JP | 2004-123742 A | 4/2004 |
| JP | 2004-352670 A | 12/2004 |
| WO | 95/31447 A1 | 11/1995 |

OTHER PUBLICATIONS

Konishi Chemical Ind. Co., Ltd., home page [retrieved Jul. 29, 2005], internet <URLl>: http://www.konishi-chem.co.jp/cgi-data/jp/pdf/pdf_2.pdf>.
Shikoku Chemicals Corporation home page [retrieved Jul. 29, 2005], internet <URL: http://www.shikoku.co.jp/chem/labo/benzo/main.html>.
Hayakawa, et al., "The Curing Reaction of 3-aryl Substituted Benzoxazine," High Perform. Polym. 12 (2000) pp. 237-246.
Furukawa, et al., "Hardening Temperature and Heat-Resistance Properties of Benzoxazine Resin," Journal of the Adhesion Society of Japan, vol. 39, No. 11 (2003) pp. 416-422. English Abstract.

*Primary Examiner* — Duc Truong
(74) *Attorney, Agent, or Firm* — Sughrue Mion, PLLC

(57) ABSTRACT

The object of the present invention is to provide a thermosetting compound having dielectric properties, in particular permittivity and dielectric loss, which are improved compared to prior art, a composition containing the same, and a molded article. The thermosetting compound according to the present invention is a dihydro benzoxazine compound represented by the following Formula (2), (2)

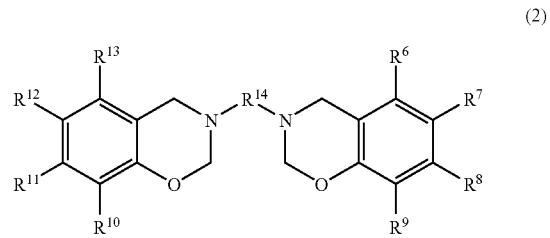

where, $R^6$ to $R^{13}$ represent a hydrogen atom, an alkyl group, or the like, and $R^{14}$ represents a divalent saturated alicyclic hydrocarbon group having a condensed ring structure.

3 Claims, No Drawings

THERMOSETTING COMPOUND, COMPOSITION CONTAINING THE SAME, AND MOLDED ARTICLE

CROSS-REFERENCES

This application claims priority from Japanese Patent Application No. 2005-228737, filed on Aug. 5, 2005, the contents of which are incorporated herein.

BACKGROUND

The present invention relates to a thermosetting compound, a composition containing the same and a molded article using the same.

In prior art, thermosetting resins such as phenol resin, melamine resin, epoxy resin, unsaturated polyester resin and bis-maleimide resin have been used widely in a variety of applications in a variety of industrial fields, from the viewpoints of excellent heat resistance, reliability and the like. In particular, regarding thermosetting resin used as electronic material application (for instance, substrate material), so as to respond to higher densification (miniaturization) of electronic apparatus/component and faster speed of communication signal in recent years, improvement of signal communication speed and high frequency properties by amelioration of dielectric properties (decrease in permittivity and decrease in dielectric loss) is desired.

The dihydro benzoxazine compounds represented by the following Formula (3) and Formula (4) are known as source materials of thermosetting resin having such excellent dielectric properties (for instance, refer to Non-patent Documents 1 and 2).

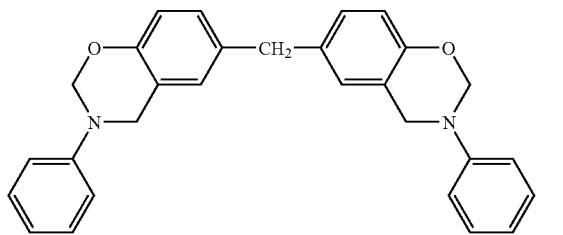

(3)

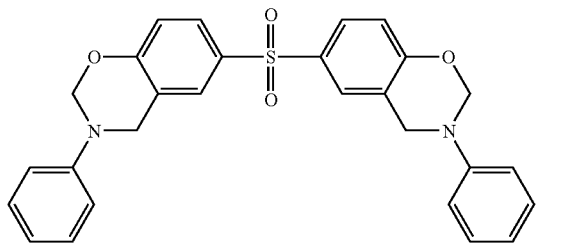

(4)

A resin obtained by ring-opening polymerization of benzoxazine ring of such dihydro benzoxazine compound is accompanied by no concomitant generation of volatile constituent at heat curing time, and also has excellent flame resistance and water resistance.

Note that, as prior art related to thermosetting resin having a dihydro benzoxazine (hereinafter also referred to as simply "benzoxazine") structure, those indicated below exist.

A specific benzoxazine structure is disclosed in Patent Document 1.

In addition, a benzoxazine structure formed with an aromatic amine (aniline), with a permittivity (1 MHz) of 3.06 to 3.71, is disclosed in Patent Document 2.

In addition, it is stated in Patent Document 3 and Non-patent Document 3 that using an aliphatic amine in the formation of a resin having a benzoxazine ring leads to poor heat resistance of the cured article.

In addition, curing temperature properties and heat resistance of bifunctional benzoxazine resin are disclosed in Non-patent Document 4.

[Non-patent Document 1] Konishi Chemical Ind. Co., Ltd. home page [retrieved 29 Jul. 2005], internet <URL: http://www.konishi-chem.co.jp/cgi-data/jp/pdf/pdf_2.pdf>
[Non-patent Document 2] Shikoku Chemicals Corporation home page [retrieved 29 Jul. 2005], internet <URL: http://www.shikoku.co.jp/chem/labo/benzo/main.html>
[Patent Document 1] Japanese Patent Application Laid-open No. S49-47378
[Patent Document 2] Japanese Patent Application Laid-open No. 2000-154225
[Patent Document 3] Japanese Patent Application Laid-open No. H8-183835
[Non-patent Document 3] High Perform. Polym. 12 (2000) 237-246. Printed in the UK
[Non-patent Document 4] Journal of the Adhesion Society of Japan Vol. 39 No. 11 (2003) 416-422.

SUMMARY

However, although the prior art dihydro benzoxazin a compound represented by (3) above has, as described above, excellent dielectric properties among thermosetting resins, even higher dielectric properties are desired in response to the latest even higher performance of electronic apparatus/component. For instance, regarding resin material of multilayered substrate constituting the package of ICs such as memories and logical processors, demanded as properties at 100 MHz and 1 GHz at an ambient temperature of 23° C. are a permittivity of 3.5 or less, as well as, under identical conditions, a value of 0.015 or less for the dielectric tangent, which is an indicator of dielectric loss. Also, prior art dihydro benzoxazine compound represented by (4) has inadequate permittivity of 4.4.

In addition, from the technical trends expected in the future, the tendency is a demand for even lower dielectric loss. That is to say, since dielectric loss only tends to be proportional to frequency and the dielectric tangent of material in general, as the frequency used in electronic apparatus/component tends to be higher and higher, demand for material with lower dielectric tangent becomes higher.

Thus, devised in consideration of such circumstance, it is an object of the present invention to provide a thermosetting compound allowing a thermosetting resin to be formed, having properties, in particular, dielectric permittivity and dielectric loss, further improved compared to prior art, and a composition containing the same, as well as a molded article obtained therefrom.

In addition, solder heat resistance may be cited as a required property with respect to materials used around the substrate. Also in this regard, as applicability will be necessary in the future to cases where lead-free solder is used, the demands with respect to heat resistance tend to be more stringent than in prior art.

Thus, taking this point into consideration as well, it is an[other] object of the present invention to provide a thermosetting compound allowing heat resistance to be increased without undermining dielectric properties, and a composition containing the same, as well as a molded article obtained therefrom.

As a result of earnest studies on a variety of dihydro benzoxazine compounds and open-ring polymers thereof to solve the above issues, the present inventors discovered that a resin molded article obtained from a compound having nitrogens of dihydro benzoxazine rings bonded to one another by a specific hydrocarbon group, or the like, had extremely good dielectric properties, and reached completion of the present invention.

Concretely, from aliphatic diamines conventionally said to have poor heat resistance, specific ones were selected to form a benzoxazine structure, which was found to have an equivalent heat resistance to aromatic benzoxazine structures from the point of view of solder heat resistance, and furthermore, low permittivity.

That is to say, the thermosetting compound according to the present invention is a dihydro benzoxazine compound synthesized from a phenol compound represented by the following Formula (1), a saturated alicyclic hydrocarbon diamine compound having a condensed ring structure, and an aldehyde compound.

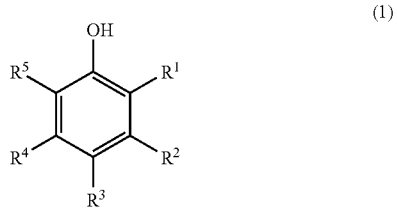

(1)

Herein, $R^1$ to $R^5$ in Formula (1) represent a hydrogen atom, an alkyl group, an aryl group, an aryl alkyl group, an alkoxy group, or a cyano group, any of which may be identical or different. With the proviso that at least either one of $R^1$ and $R^5$ is a hydrogen atom.

In other words, the thermosetting compound of the present invention obtained in this way is a bifunctional dihydro benzoxazine compound represented by the following Formula (2):

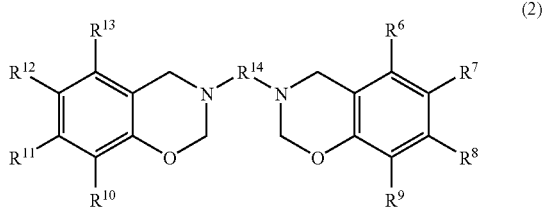

(2)

Herein, $R^6$ to $R^{13}$ in Formula (2) represent a hydrogen atom, an alkyl group, an aryl group, an aryl alkyl group, an alkoxy group, or a cyano group, any of which may be identical or different, and $R^{14}$ represents a divalent saturated alicyclic hydrocarbon group having a condensed ring structure.

According to the observations of the present inventors, a resin molded article obtained by ring-opening polymerization of benzoxazine ring of such a thermosetting compound was confirmed to present sufficient dielectric properties and heat resistance required as an electronic material.

In particular, regarding dielectric properties, one of the main causes is thought to be a wide intermolecular spacing maintained by having a rigid alicyclic hydrocarbon group such as [the one] represented by group $R^{14}$ between a ring-opened benzoxazine and a ring-opened benzoxazine, lowering the density of the molded article as a whole. However, as described later, the permittivity of the obtained molded article in the high frequency band regions of 100 MHz and 1 GHz is remarkably decreased, to about 3 or lower, and although the detail of the reason is still unclear, it is difficult to think that this is caused simply by the lower density.

In addition, when the dielectric loss of the molded article obtained in this way was measured and evaluated in detail, the value of the dielectric tangent was found to decrease remarkably compared to prior art. Consequently, a factor exerting some further action is thought to exist in the dielectric properties, in particular the decrease in dielectric loss, of the thermosetting dihydro benzoxazine compound according to the present invention.

Although the detail of the mechanism exerting such an action is also still not clear, the thermosetting compound according to the present invention has nitrogen atoms of dihydro benzoxazine rings bonded to one another by the residue of the amines of a saturated alicyclic hydrocarbon diamine compound having a condensed ring structure, that is to say, a divalent saturated alicyclic hydrocarbon group having a condensed ring structure represented by the $R^{14}$ above, for this reason, the configurational distribution of the benzene rings in the resin molecule formed by ring-opening polymerization of dihydro benzoxazine ring is expected to be different from that in prior art, and this difference in configurational distribution is assumed to be contributing to the remarkable decrease in dielectric loss. With the proviso that the action is not limited to this.

In addition, regarding applicability to lead-free solder process, which may become highly desired in the future, from the point of view of improving even further the heat resistance along with dielectric properties, diamine compounds having a saturated alicyclic hydrocarbon group having a condensed ring structure are desirable, among which 3(4),8(9),-bis(aminomethyl)tricyclo[5,2,1,0$^{2,6}$]decane, 2,5(6)-bis(aminomethyl)bicyclo[2,2,1]heptane, or 1,3-diamino adamantane is even more desirable.

In addition, the composition according to the present invention is one that contains the thermosetting compound of the present invention and is especially useful as a source composition for resin materials requiring dielectric properties, in particular low permittivity and low dielectric loss, as well as heat resistance. In addition, the molded article according to the present invention is one that is obtained by heat curing a composition containing the thermosetting compound of the present invention, for this reason, significant improvement of signal communication speed and high frequency properties, and application to lead-free solder process can be intended.

The thermosetting compound of the present invention is synthesized from a phenol compound represented by Formula (1), a saturated alicyclic hydrocarbon diamine compound having a condensed ring structure, and an aldehyde compound, and by having a molecular structure represented by Formula (2), allows the dielectric properties, in particular permittivity and dielectric loss, of a molded article obtained from this thermosetting compound or a composition containing the same to be remarkably more improved than in prior art, moreover, sufficient heat resistance to be achieved without undermining such dielectric properties. As a result, even higher performance of electronic apparatus/component and the like, using this molded article can be realized.

DETAILED DESCRIPTION

Hereinafter, embodiments of the present invention will be described in detail.

<I. Thermosetting Compound>

The thermosetting compound according to the present invention is a dihydro benzoxazine compound synthesized from (A) a specific phenol compound, (B) a saturated alicyclic hydrocarbon diamine compound and (C) an aldehyde compound.

[(A) Specific Phenol Compound]

As described above, the specific phenol compound is a monovalent compound represented by Formula (1) above, in other words, a compound having one phenolic hydroxyl group and at least one ortho position being a hydrogen atom, for instance, phenol, o-cresol, m-cresol, p-cresol, 3,4-xylenol, nonyl phenol, p-t-butyl phenol, p-octyl phenol, 4-cyano phenol, and the like, may be cited.

[(B) Saturated Alicyclic Hydrocarbon Diamine Compound Having a Condensed Ring Structure]

Although saturated alicyclic hydrocarbon diamine compounds having a condensed ring structure are not limited in particular, from the point of view of heat resistance improvement, diamine compounds having an alicyclic hydrocarbon group having a condensed ring structure, such as, norbonene backbone (bicyclo[2,2,1]heptane), dicyclopentadiene backbone (tricyclo[5,2,1,0$^{2,6}$]decane), and adamantane backbone (tricyclo 3,3,1,1$^{3,7}$]decane), may be cited. In addition, a hydrogen atom of the alicyclic hydrocarbon group of these condensed ring structures may be substituted with an alkyl group, or the like, and an alkylene group may be present between an alicyclic hydrocarbon group and the nitrogen atom of an amino group.

In addition, among these saturated alicyclic hydrocarbon diamine compounds having a condensed ring structure, from the point of view of obtaining a thermosetting compound for forming a molded article with even better dielectric properties and more improved heat resistance, more desirable is 3(4),8(9),-bis(aminomethyl)tricyclo[5,2,1,0$^{2,6}$]decane, 2,5(6)-bis(aminomethyl)bicyclo[2,2,1]heptane, or 1,3-diamino adamantane.

[(C) Aldehyde Compound]

Aldehyde compounds are not limited in particular and, for instance formaldehydes, acetaldehyde, benzaldehyde and the like may be given, among which formaldehydes are preferred, and concretely, using formalin, which is an aqueous solution of formaldehyde, and paraformaldehyde, which is a polymerized formaldehyde, is desirable.

[Method for Synthesizing Thermosetting Compound]

The thermosetting compound according to the present invention is one that is synthesized by reacting 2 molar equivalents of the above (A) specific phenol compound, 1 molar equivalent of (B) saturated alicyclic hydrocarbon diamine having a condensed ring structure, and 4 molar equivalents of (C) aldehyde compound, and any well known method may be adopted as the synthesis method thereof.

For instance, synthesis is possible easily by mixing 2 molar equivalents of (A) specific phenol compound, 1 molar equivalent of (B) saturated alicyclic hydrocarbon diamine having a condensed ring structure, and 4 molar equivalents of (C) aldehyde compound, and stirring on the order of 10 minutes to one hour while heating to 100 to 130° C.

Alternatively, synthesis may be by dissolving the above-mentioned constituents (A) to (C) in a halogenated solvent such as chloroform, methylene chloride, dichloroethane or trichloroethane, an aromatic series solvent such as benzene, toluene or xylene, a lower alcohol such as methanol, ethanol, propanol or butanol, or a solvent such as 1,4-dioxane, ethylene glycol monomethyl ether, ethylene glycol monoethyl ether or ethylene glycol monobutyl ether.

In this case, reacting on the order of 1 to 20 hours while heating to 50 to 130° C. is sufficient, the solvent is eliminated after the end of the reaction, and as necessary, unreacted (A) specific phenol compound, (B) saturated alicyclic hydrocarbon diamine having a condensed ring structure, and (C) aldehyde compound may be eliminated by washing with alkali water solution or an alcohol such as methanol or ethanol.

In this way, the bifunctional dihydro benzoxazine compound represented by Formula (2) above can be obtained. Thus, group $R^{14}$ bonding the nitrogen atoms of the dihydro benzoxazine rings in Formula (2) to one another is a residue of the amines of the (B) saturated alicyclic hydrocarbon diamine compound having a condensed ring structure mentioned above (that is to say, a divalent saturated alicyclic hydrocarbon group having a condensed ring structure), and becomes one corresponding to the saturated alicyclic hydrocarbon diamine having a condensed ring structure compound used for the synthesis.

That is to say, group $R^{14}$ is not limited in particular, for instance, alicyclic hydrocarbon groups having a condensed ring structure such as, substituted or unsubstituted divalent norbonene backbone (bicyclo[2,2,1]heptane), dicyclopentadiene backbone (tricyclo[5,2,1,0$^{2,6}$]decane), and adamantane backbone (tricyclo 3,3,1,1$^{3,7}$]decane) may be cited.

In addition, among these alicyclic hydrocarbon groups having a condensed ring structure, from the point of view of possibly improving heat resistance along with the dielectric properties of the thermosetting compound represented by Formula (2), more desirable are 3(4),8(9),-bis(aminomethyl) tricyclo[5,2,1,0$^{2,6}$]decane, 2,5(6)-bis(amino methyl)bicyclo [2,2,1]heptane, and 1,3-diamino adamantane.

In addition, the structure of the present thermosetting compound can be detected with and inferred from NMR, UV, IR, Raman spectrometry, SIMS, TOF-SIMS, GC-MS, pyrolysis MS and other methods.

<II. Composition>

The composition according to the present invention is one containing the thermosetting compound of the present invention mentioned above preferably as the main component, and, for instance, one containing the thermosetting compound of the present invention as the main component, and another thermosetting resin as a secondary constituent, may be cited.

As another thermosetting resin that is a secondary constituent, for instance, epoxy series resin, thermoset type modified polyphenylene ether resin, thermoset type polyimide resin, silicone, benzoxazine resin, melamine resin, urea resin, allyl resin, phenol resin, unsaturated polyester resin, bis-maleimide triazine resin, alkyd resin, furan resin, polyurethane resin, aniline resin, and the like, may be cited. Among these, point of view of further improving the heat resistance of the molded article formed from this composition, epoxy series resin and thermoset type polyimide resin are more desirable. These other thermosetting resins may be used alone or two species or more may be used in combination.

In addition, the composition according to the present invention, as necessary, may contain various additives such as fire retardant, nucleant, oxidation inhibitor (senescence prevention agent), heat stabilizer, light stabilizer, ultraviolet light absorbent, lubricant, fire-resistance helper, electrostatic preventer, antifog, filler, softener, plasticizer and pigment. These may be respectively used alone or two species or more may be used in combination.

<III. Molded Article>

The molded article according to the present invention is one obtained by heat curing of the thermosetting compound of the present invention, or the composition of the present invention containing the same, and is a resin molded article comprising a ring-opening polymerization of the dihydro benzoxazine compound represented by Formula (2). In addition, the dimensions and shape thereof are not limited in particular confinement, for instance, sheet form (board), block form, and the like, may be cited, and furthermore, may be provided with another site (for instance, an adhesive layer).

As method for ring-opening polymerization thereof, any well known prior art polymerization method can be used, and generally, heating at on the order of 120 to 260° C. for several hours is sufficient; however if the heating temperature is lower or the heating time is insufficient, depending on the circumstance, sometimes curing is insufficient and mechanical strength becomes insufficient. In addition, if the heating temperature is excessively higher, or the heating time is too long, depending on the circumstance, sometimes a secondary reaction such as decomposition occurs, disadvantageously decreasing the mechanical strength. Thus, it is desirable to select conditions that are suitable to the type of thermosetting compound used.

In addition, when carrying out ring-opening polymerization, a suitable cure promoter may be added. As such cure promoter, any cure promoter generally used when ring-opening polymerizing a dihydro benzoxazine compound can be used, and for instance, multifunctional phenols such as catechol and bis-phenol A, sulfonic acids such as p-toluene sulfonic acid and p-phenol sulfonic acid, carboxylic acids such as benzoic acid, salicylic acid, oxalic acid and adipic acid, metal complexes such as cobalt(II) acetyl acetonate, aluminum(III) acetyl acetonate and zirconium(IV) acetyl acetonate, metal oxides such as calcium oxide, cobalt oxide, magnesium oxide and iron oxide, calcium hydroxide, imidazole and derivatives thereof, tertiary amines such as diaza bicyclo undecene and diaza bicyclo nonene, and salts thereof, phosphorus series compounds such as triphenyl phosphine, triphenyl phosphine-benzoquinone derivatives, triphenyl phosphine-triphenyl boron salt and tetraphenyl phosphonium-tetraphenyl borate, and derivatives thereof, may be cited. These may be used alone or two species or more may be mixed and used.

The amount of cure promoter added is not limited in particular; however, if the amount added becomes excessive, sometimes the permittivity and dielectric tangent of the molded article increase, deteriorating dielectric properties, exerting detrimental effects on mechanical physical properties, such that generally, it is desirable to use the cure promoter in proportions with respect to 100 weight parts of the above-mentioned thermosetting compound of the present invention, of preferably 5 weight parts or less, and more preferably 3 weight parts or less.

As described above, the molded article of the present invention obtained in this way, having a rigid alicyclic hydrocarbon group such as represented by group $R^{14}$ between a ring-opened benzoxazine and a ring-opened benzoxazine allows extremely good dielectric properties to be realized, owing mainly to a lower density by augmentation of intermolecular spacing and some other factor, and furthermore, to the influence of the configurational distribution of intramolecular benzene rings.

In addition, the molded article of the present invention, based on a property called thermosettability of other thermosetting resin contained in the thermosetting compound of the present invention and composition, has excellent heat resistance, reliability, flame resistance, formability, aesthetic, and the like, moreover, as the glass transition temperature (Tg) is high, it can be applied in sites subject to stress and in flexible regions, and is also desirable in terms of health management, as it does not generate volatile by-products during polymerization and such volatile by-products do not remain inside the molded article.

EXAMPLES

Hereinafter, the present invention will be described in further details by means of examples; however, the present invention is not limited to these examples only.

Example 1

Thermosetting Compound

One mole of 3(4),8(9),-bis(aminomethyl)tricyclo[5,2,1,0$^{2,6}$]decane as saturated alicyclic hydrocarbon diamine compound having a condensed ring structure, two moles of phenol as the phenol compound represented by Formula (1), as well as, 4 moles of paraformaldehyde as aldehyde compound and 1500 g of chloroform were mixed. This mixture was heated to 60° C. under stirring, and the reaction was carried out for 6 hours since chloroform started circulating. After the end of the reaction, the reaction mixture was washed with an aqueous solution of 1 N sodium hydroxide, and then rinsed with ion exchanged water. Then, after the chloroform phase was dried with anhydrous sodium sulfate, chloroform was evaporated with a rotary evaporator to obtain a bifunctional dihydro benzoxazine compound in which $R^{14}$ of Formula (2) is the amino residue of 3(4),8(9),-bis(aminomethyl)tricyclo[5,2,1,0$^{2,6}$]decane.

Example 2

Thermosetting Compound

A bifunctional dihydro benzoxazine compound, in which $R^{14}$ of Formula (2) is the amino residue of 2,5(6)-bis(aminomethyl)bicyclo[2,2,1]heptane, was obtained similarly to Example 1, except that 2,5(6)-bis(aminomethyl)bicyclo[2,2,1]heptane ("NBDA", manufactured by Mitsui Chemicals Inc.) was used as saturated alicyclic hydrocarbon diamine compound and the overall scale was changed to 0.8 fold.

Comparative Example 1

Thermosetting Compound

A bifunctional dihydro benzoxazine compound, in which $R^{14}$ of Formula (2) is the amino residue of 1,2-diaminoethane, was obtained similarly to Example 1, except that one mole of 1,2-diaminoethane was used as saturated aliphatic hydrocarbon diamine compound.

Comparative Example 2

Thermosetting Compound

A bifunctional dihydro benzoxazine compound, in which $R^{14}$ of Formula (2) is the amino residue of 1,6-diaminohexane, was obtained similarly to Example 1, except that one mole of 1,6-diaminohexane was used as saturated aliphatic hydrocarbon diamine compound.

Examples 3 and 4, Comparative Examples 3 and 4

Molded Article

The bifunctional dihydro benzoxazine compounds obtained in Examples 1 and 2 and Comparative Examples 1 and 2 were supplied to a press machine, and by applying a pressure of 3 MPa and heating for one hour at 140° C., then one hour at 160° C., and finally one hour at 180° C., to carry out ring-opening polymerization, 60 mm long, 60 mm wide and 0.5 mm thick sheet-form molded articles were obtained.

<Measurement of Dielectric Properties>

The sheet-form molded articles obtained in Examples 3 and 4 and Comparative Examples 3 and 4 were cut to 15 mm×15 mm to prepare measurement samples, each measurement sample was supplied to a permittivity meter (product name "RF Impedance/Material Analyzer E4991A", manufactured by AGILENT), and permittivity and dielectric tangent were measured by the capacity method, at 23° C., 100 MHz and 1 GHz. The obtained results are summarized and shown in Table 1.

<Measurement of Thermostability>

The sheet-form molded articles obtained in Examples 3 and 4 and Comparative Examples 3 and 4 were cut, 10% weight loss temperature (Td10) was measured in order to evaluate the weight under air by the TGA (Thermo Gravimetric Analysis) method, with a DTG-60 manufactured by Shimadzu. The obtained results are shown together in Table 1.

TABLE 1

| Molded article | 100 MHz | | 1 GHz | | Td5 | Td10 |
| --- | --- | --- | --- | --- | --- | --- |
| | Permittivity | Dielectric tangent | Permittivity | Dielectric tangent | | |
| Example 3 (tcd) | 2.86 | 0.0035 | 2.85 | 0.0031 | 296° C. | 362° C. |
| Example 4 (NB) | 2.85 | 0.0037 | 2.84 | 0.0036 | 263° C. | 362° C. |
| Comparative Example 3 (c2) | 3.24 | 0.0061 | 3.22 | 0.0060 | 257° C. | 302° C. |
| Comparative Example 4 (c6) | 3.00 | 0.0049 | 2.99 | 0.0045 | 266° C. | 282° C. |

In addition, the obtained resin composition stretching with respect to temperature was measured with a DMS6100, manufactured by SII, to evaluate CTE (=α). α was measured at 23° C. to 150° C.

The obtained results were, regarding Example 3, CTE was 62 ppm/° C., and regarding Comparative Example 4, 101 ppm/° C.

Conforming to "JISC6471 Test Method For Copper Clad Laminate For Flexible Printed Wiring Board", a base film was floated for 5 seconds in a solder bath at 260° C., and whether or not a bulge was present was visually inspected. The determination was carried out as, a cross if a bulge was present, and a circle if there was no bulge. As a result, Examples 3 and 4 were circles by the above test, and Comparative Examples 3 and 4 were crosses.

In addition, when an identical test was carried out with the above-mentioned 5 seconds turned into 20 seconds, Examples 3 and 4 were circles by the above test, and Comparative Examples 3 and 4 were crosses.

According to the thermosetting compound of the present invention, composition, and molded article containing the same, the dielectric properties, in particular permittivity and dielectric loss, being remarkably improved compared to prior art, furthermore, sufficient heat resistance being provided, broad employment is possible in electronic component/apparatus and materials therefor, and in particular, in applications for which excellent dielectric properties are required, such as multilayered substrate, laminate, sealant and adhesive.

We claim:

1. A thermosetting compound synthesized from a phenol compound represented by the following Formula (1)

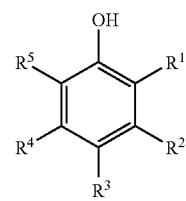

(1)

(in Formula (1), $R^1$ to $R^5$ represent a hydrogen atom, an alkyl group, an aryl group, an aryl alkyl group, an alkoxy group, or a cyano group, any of which may be identical or different, with the proviso that at least either one of $R^1$ and $R^5$ is a hydrogen atom), a saturated alicyclic hydrocarbon diamine compound having a condensed ring structure, and an aldehyde compound.

2. The thermosetting compound according to claim 1, wherein said saturated alicyclic hydrocarbon diamine compound is 3(4),8(9),-bis(aminomethyl)tricyclo[5,2,1,0$^{2,6}$]decane,2,5(6)-bis(aminomethyl)bicyclo [2,2,1]heptane or 1,3-diamino adamantane.

3. A composition containing the thermosetting compound according to claim 1.

* * * * *